(12) United States Patent
Bartling et al.

(10) Patent No.: US 10,490,299 B2
(45) Date of Patent: Nov. 26, 2019

(54) IDENTIFICATION OF TRAITS ASSOCIATED WITH DNA SAMPLES USING EPIGENETIC-BASED PATTERNS DETECTED VIA MASSIVELY PARALLEL SEQUENCING

(71) Applicant: Battelle Memorial Institute, Columbus, OH (US)

(72) Inventors: Craig M. Bartling, Lewis Center, OH (US); Mark E. Hester, Reynoldsburg, OH (US); Esley M. Heizer, Galloway, OH (US)

(73) Assignee: Battelle Memorial Institute, Columbus, OH (US)

( * ) Notice: Subject to any disclaimer, the term of this patent is extended or adjusted under 35 U.S.C. 154(b) by 780 days.

(21) Appl. No.: 14/732,244

(22) Filed: Jun. 5, 2015

(65) Prior Publication Data

US 2015/0354002 A1 Dec. 10, 2015

Related U.S. Application Data

(60) Provisional application No. 62/008,650, filed on Jun. 6, 2014.

(51) Int. Cl.
| | | |
|---|---|---|
| *C12Q 1/68* | (2018.01) | |
| *G16B 40/00* | (2019.01) | |
| *G16B 20/00* | (2019.01) | |
| *C12Q 1/6869* | (2018.01) | |

(52) U.S. Cl.
CPC ............. *G16B 40/00* (2019.02); *G16B 20/00* (2019.02); *C12Q 1/6869* (2013.01)

(58) Field of Classification Search
None
See application file for complete search history.

(56) References Cited

U.S. PATENT DOCUMENTS

| | | | |
|---|---|---|---|
| 2012/0003634 A1* | 1/2012 | Frumkin | C12Q 1/6858 435/6.11 |
| 2013/0078626 A1 | 3/2013 | Wasserstrom et al. | |
| 2015/0005176 A1* | 1/2015 | Kim | G16B 30/00 506/2 |
| 2015/0100244 A1* | 4/2015 | Hannum | G16B 20/00 702/19 |

FOREIGN PATENT DOCUMENTS

| | | | | |
|---|---|---|---|---|
| WO | WO-2011070441 A2 * | 6/2011 | | C12Q 1/6881 |

OTHER PUBLICATIONS

D. Frumkin et al., "DNA Methylation-Based Forensic Tissue Identification," Forensic Sci. Int'l: Genetics 2010, 8 pages.

* cited by examiner

*Primary Examiner* — Stephanie K Mummert
(74) *Attorney, Agent, or Firm* — Barnes & Thornburg LLP

(57) ABSTRACT

Illustrative embodiments of systems and methods for the identification of traits associated with DNA samples using epigenetic-based patterns detected via massively parallel sequencing (MPS) are disclosed. Illustrative embodiments may involve digesting a DNA sample with a methylation-dependent endonuclease, amplifying loci of the digested DNA sample (including a positive control locus that does not contain a restriction site for the methylation-dependent endonuclease) using a multiplex PCR to produce amplicons, sequencing the amplicons using an MPS instrument to generate sequence reads, determining a sequence count for each of the loci by comparing each of the sequence reads to reference sequences, normalizing the sequence count for each of the loci to the sequence count of the positive control locus, and identifying a trait associated with the DNA sample by applying a classification algorithm to the normalized sequence counts.

33 Claims, 4 Drawing Sheets

Specification includes a Sequence Listing.

SEQUENCE LISTING

<160> NUMBER OF SEQ ID NOS: 20

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcagcaggcc gcggagaag                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agcagctgtg ccgggccag                                                  19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagcaacagc acccagcttg                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacaggctca gtcgcggatc                                                 20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggaaacctc agtagcaaaa ttg                                             23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgagacttt aggtgtgcat c                                               21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgtaggctgc ggtgagctc                                                   19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatccatgcc cgctgggatg                                                  20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagcctagac gtcaagttac ag                                               22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgacctccg gatccaactg                                                  20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgcatggtg tctggtactt c                                                21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaagctctcg tggactactt g                                                21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
cagcctgctc ttcactgcag                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
agaggccgat gaagccgtag                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
aagggcagag ttccgctgtc                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
cggatgcagg aggatcctag                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gcgaaggaag tgctggagtc                                                    20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gtttcttgaa agggccagac ac                                                 22

```
<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caaagtactg gggttacagg tg                                                 22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggatgaacct ttaagacatc atc                                                23
```

IDENTIFICATION OF TRAITS ASSOCIATED WITH DNA SAMPLES USING EPIGENETIC-BASED PATTERNS DETECTED VIA MASSIVELY PARALLEL SEQUENCING

CROSS REFERENCE TO RELATED APPLICATION

This application claims the benefit of U.S. Provisional Patent Application No. 62/008,650, filed Jun. 6, 2014, the entire disclosure of which is incorporated by reference herein.

SEQUENCE LISTING

The instant application contains a Sequence Listing which has been submitted electronically in ASCII format and is hereby incorporated by reference in its entirety. Said ASCII copy, created on Jul. 20, 2015, is named 920006-237744_SL.txt and is 4,927 bytes in size.

TECHNICAL FIELD

The present disclosure relates, generally, to the identification of traits associated with deoxyribonucleic acid (DNA) samples and, more particularly, to the identification of traits associated with DNA samples using epigenetic-based patterns detected via massively parallel sequencing (MPS) (sometimes referred to in the art as "next-generation sequencing").

BACKGROUND

The ability to determine the source of biological materials from evidence samples can be highly informative for interpreting forensic data. While methods to evaluate the source of a sample have matured over time, prior art methods have suffered from lack of sensitivity in degraded samples, reproducibility, ease of use, consumption of precious samples, inter-operator and interpretation variability. Recently, epigenetic-based methods for the determination of tissue source using capillary electrophoresis (CE) have been proposed, as described in U.S. Patent Application Publication Nos. 2012/0003634 and 2013/0078626, the entire disclosures of which are incorporated by reference herein. While these CE-based methods show increased sensitivity and specificity, they are not readily adapted for use with MPS-based workflows.

SUMMARY

According to one aspect, a method may comprise digesting a DNA sample with a methylation-dependent endonuclease; amplifying a plurality of loci of the digested DNA sample using a multiplex polymerase chain reaction (PCR) to produce a plurality of amplicons, at least one of the plurality of loci being a positive control locus that does not contain a restriction site for the methylation-dependent endonuclease; sequencing the plurality of amplicons using a massively parallel sequencing (MPS) instrument to generate a plurality of sequence reads; determining a sequence count for each of the plurality of loci by comparing each of the plurality of sequence reads to a plurality of reference sequences, each of the plurality of reference sequences being associated with one of the plurality of loci; normalizing the sequence count for each of the plurality of loci to the sequence count of the positive control locus; and identifying a trait associated with the DNA sample by applying a classification algorithm to the normalized sequence counts.

In some embodiments, comparing each of the plurality of sequence reads to the plurality of reference sequences may comprise determining whether each of the plurality of sequence reads sufficiently aligns with any of the plurality of reference sequences. In other embodiments, comparing each of the plurality of sequence reads to the plurality of reference sequences may comprise determining whether each of the plurality of sequence reads exactly matches any of the plurality of reference sequences.

In some embodiments, the multiplex PCR may use unlabeled primers. The method may further comprise removing amplicons having a length that is outside a predetermined range prior to sequencing the plurality of amplicons. The predetermined range may be about 50 base pairs to about 500 base pairs.

In some embodiments, applying the classification algorithm may comprise applying a k-Nearest Neighbor (k-NN) algorithm. Applying the k-NN algorithm may comprise computing un-weighted Euclidean distances of normalized sequence counts between the DNA sample and a plurality of reference samples associated with different traits.

In some embodiments, the method may further comprise labeling each of the plurality of amplicons with a unique nucleotide index, mixing the plurality of amplicons with additional amplicons that have each been labeled with a unique nucleotide index, and sequencing the additional amplicons using the MPS instrument at the same time as sequencing the plurality of amplicons. The additional amplicons may contain short tandem repeats that are used to allelotype the DNA sample. The additional amplicons may contain single nucleotide polymorphisms that are used to allelotype the DNA sample.

In some embodiments, at least one of the plurality of loci may be a negative control locus that is substantially digested by the methylation-dependent endonuclease irrespective of the trait associated with the DNA sample. The negative control locus may be SW14. The positive control locus may be L98328. The methylation-dependent endonuclease may be Hha1. The plurality of loci may be L91762, L68346, L50468, L14432, L4648, L62086, L76138, and L36599.

In some embodiments, identifying the trait associated with the DNA sample may comprise any of identifying a tissue source from which the DNA sample was derived, determining whether the tissue source is blood, skin, saliva, or semen, identifying a cell type from which the DNA sample was derived, identifying an age of an organism from which the DNA sample was derived, identifying a disease state or risk of disease of an organism from which the DNA sample was derived, identifying a response to environmental signals of an organism from which the DNA sample was derived, identifying a body mass index or an obesity state of an organism from which the DNA sample was derived, identifying an expression level of one or more genes in an organism from which the DNA sample was derived, identifying a physical characteristic of an organism from which the DNA sample was derived, identifying a drug response of an organism from which the DNA sample was derived, identifying an epigenetic inheritance of an organism from which the DNA sample was derived, and identifying whether the DNA sample was synthesized in vitro.

According to another aspect, one or more non-transitory, computer-readable media comprising a plurality of instructions that, when executed by one or more processors, causes the one or more processors to determine a sequence count for each of a plurality of loci of a digested deoxyribonucleic acid (DNA) sample by comparing each of a plurality of sequence reads to a plurality of reference sequences, the plurality of sequence reads resulting from massively parallel sequencing (MPS) of amplification products of a multiplex polymerase chain reaction (PCR) applied to the plurality of loci, wherein (i) the DNA sample has been digested with a methylation-dependent endonuclease, (ii) at least one of the plurality of loci is a positive control locus that does not contain a restriction site for the methylation-dependent endonuclease, and (iii) each of the plurality of reference sequences is associated with one of the plurality of loci; normalize the sequence count for each of the plurality of loci to the sequence count of the positive control locus; and apply a classification algorithm to the normalized sequence counts to identify a trait associated with the DNA sample.

In some embodiments, the plurality of instructions may cause the one or more processors to determine whether each of the plurality of sequence reads sufficiently aligns with any of the plurality of reference sequences to determine the sequence count for each of the plurality of loci. In other embodiments, the plurality of instructions may cause the one or more processors to determine whether each of the plurality of sequence reads exactly matches any of the plurality of reference sequences to determine the sequence count for each of the plurality of loci. In some embodiments, the plurality of instructions may cause the one or more processors to compute un-weighted Euclidean distances of normalized sequence counts between the DNA sample and a plurality of reference samples associated with different traits as part of the classification algorithm.

BRIEF DESCRIPTION OF THE DRAWINGS

The concepts described in the present disclosure are illustrated by way of example and not by way of limitation in the accompanying figures. For simplicity and clarity of illustration, elements shown in the figures are not necessarily drawn to scale. Where considered appropriate, reference labels may be repeated among the figures to indicate corresponding or analogous elements. The detailed description particularly refers to the accompanying figures in which.

DETAILED DESCRIPTION OF THE DRAWINGS

Figure 1:
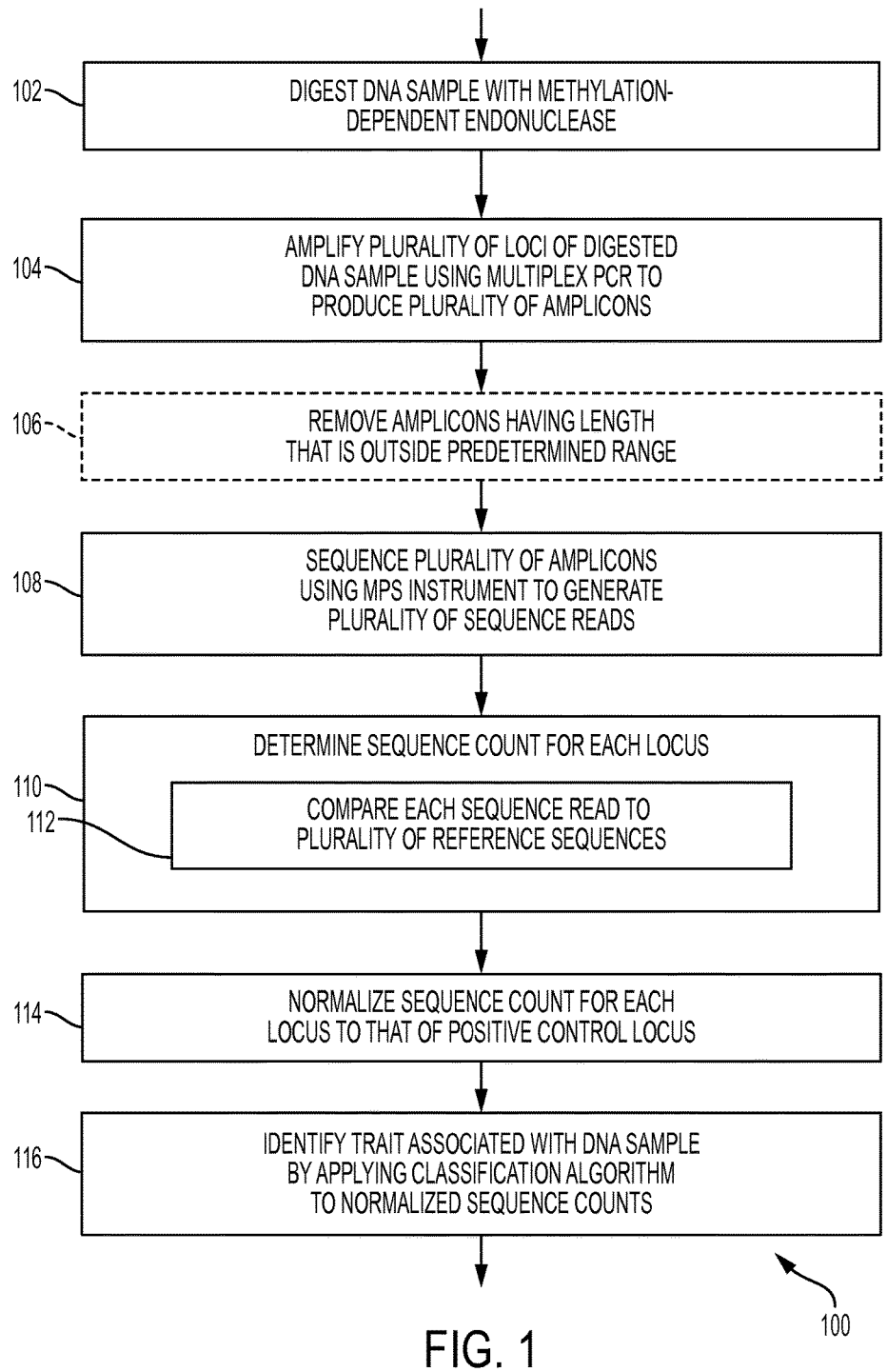
FIG. 1 is a simplified flow diagram illustrating at least one embodiment of a method of identifying a trait associated with a DNA sample using epigenetic-based patterns detected via MPS.

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the concepts described herein may be implemented in hardware, firmware, software, or any combination thereof. For instance, embodiments of the methods described herein (or portions thereof) may be implemented as instructions carried by or stored on one or more machine-readable or computer-readable storage media, which may be read and/or executed by one or more processors. A machine-readable or computer-readable storage medium may be embodied as any device, mechanism, or physical structure for storing or transmitting information in a form readable by a machine (e.g., a computing device or system). For example, a machine-readable or computer-readable storage medium may be embodied as read only memory (ROM) device(s); random access memory (RAM) device(s); magnetic disk storage media; optical storage media; flash memory devices; mini- or micro-SD cards, memory sticks, and others.

In the drawings, specific arrangements or orderings of schematic elements, such as those representing various processes and sub-processes, may be shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

In general, schematic elements used to represent processes or sub-processes may be implemented using any suitable form of machine-readable instruction, such as software or firmware applications, programs, functions, modules, routines, processes, procedures, plug-ins, applets, widgets, code fragments and/or others, and that each such instruction may be implemented using any suitable programming language, library, application programming interface (API), and/or other software development tools. For example, some embodiments may be implemented using Java, C++, and/or other programming languages. Similarly, schematic elements used to represent data or information may be implemented using any suitable electronic arrangement or structure, such as a register, data store, table, record, array, index, hash, map, tree, list, graph, file (of any file type), folder, directory, database, and/or others.

Further, in the drawings, where connecting elements, such as solid or dashed lines or arrows, are used to illustrate a connection, relationship or association between or among two or more other schematic elements, the absence of any such connecting elements is not meant to imply that no connection, relationship or association can exist. In other words, some connections, relationships or associations between elements may not be shown in the drawings so as not to obscure the disclosure. In addition, for ease of illustration, a single connecting element may be used to represent multiple connections, relationships or associations between elements. For example, where a connecting element represents a communication of signals, data, instructions, or other information, it should be understood by those skilled in the art that such element may represent one or multiple signal paths, as may be needed, to effect the communication.

As noted above, the present disclosure relates to the identification of traits associated with DNA samples using epigenetic-based patterns detected via MPS (sometimes referred to in the art as "next-generation sequencing"). In particular, the present disclosure utilizes MPS to detect methylation patterns at specific loci of a DNA sample that are indicative of one or more particular traits associated with the DNA sample (e.g., the tissue source or cell type from which the DNA sample was derived). DNA methylation is the covalent modification of the C5 position of cytosine residues in some CpG dinucleotides that can affect gene expression and is differentially observed at specific loci in different tissue types. The present disclosure involves the digestion of extracted DNA samples using a methylation-dependent endonuclease followed by polymerase chain reaction (PCR) amplification of specific genomic regions containing the methylated residues. Loci that are methylated at the restriction site are protected from enzymatic digestion (and, hence, are amplified during PCR), whereas un-methylated loci are digested (and, hence, are not amplified during PCR), thereby resulting in differential methylation patterns when the amplification products (i.e., amplicons) are sequenced.

As described in greater detail below, the presently disclosed methods have the distinct advantage of being compatible with other MPS-based analyses, protocols, and workflows currently in use and in development. Moreover, the presently disclosed methods do not require the use of fluorescently-labeled primers as part of the PCR amplification. The present disclosure will begin by generally describing methods of identifying a trait associated with a DNA sample using epigenetic-based patterns detected via MPS, with reference to FIG. 1. Next, one illustrative embodiment of such a method, using methylation patterns detected via MPS to identify a tissue source from which a DNA sample was derived, will be described with reference to FIGS. 2-4.

While the illustrative embodiment of a tissue-typing workflow will be discussed in greatest detail herein, it is contemplated that the presently disclosed methods may also form the basis of assays for many other epigenetic-based markers, which may be used to identify any number of traits associated with DNA samples. By way of example, the presently disclosed methods might also be utilized to identify: (i) a cell type from which a DNA sample was derived, (ii) an age of an organism from which a DNA sample was derived, (iii) a disease state or risk of disease of an organism from which a DNA sample was derived, (iv) a response to environmental signals of an organism from which a DNA sample was derived (e.g., changes in methylation levels resulting from different environmental exposures, such as contaminants), (v) a body mass index or an obesity state of an organism from which a DNA sample was derived, (vi) an expression level of one or more genes in an organism from which a DNA sample was derived, (vii) a physical characteristic of an organism from which a DNA sample was derived, (viii) a drug response of an organism from which a DNA sample was derived (e.g., how the organism might respond to a particular drug regiment), and/or (ix) an epigenetic inheritance of an organism from which a DNA sample was derived (e.g., to track the inheritance of a methylation level from generation to generation), among other possible traits. Furthermore, the presently disclosed methods might also be utilized to determine whether a DNA sample was synthesized in vitro, indicated by an absence of methylation (e.g., to detect sample "spoofing" for forensic purposes).

Referring now to FIG. 1, a method 100 of identifying a trait associated with a DNA sample using epigenetic-based patterns detected via MPS is shown as a simplified flow diagram. In particular, the method 100 is illustrated as a number of blocks 102-116. The method 100 begins with block 102 in which a DNA sample is digested with a methylation-dependent endonuclease. The endonuclease used in block 102 may be any endonuclease that selectively digests a restriction site depending on whether or not that restriction site is methylated. As such, in block 102, the methylation-dependent endonuclease will digest target loci that are not methylated but will not digest target loci that are methylated. Thus, block 102 will result in various levels of digestion at particular target loci, depending on the methylation levels of the target loci present in the DNA sample.

After block 102, method 100 proceeds to block 104 in which a plurality of loci of the digested DNA sample are amplified using multiplex PCR to produce a plurality of amplicons. During block 104, the digested DNA sample will be exposed to a number of primers that are configured to cause amplification of particular loci of the DNA sample (where those loci have not been digested in block 102). As noted above, due to the use of MPS (block 108), the method 100 does not require fluorescently-labeled primers to be used in block 104 (i.e., unlabeled primers may be used in block 104). The amount of amplification of each locus that occurs (and, hence, the number of amplicons produced that correspond to that locus) in block 104 will be inversely related to the amount of digestion of that locus that occurred in block 102. For instance, where a particular locus is highly-methylated and therefore only mildly digested (if at all) in block 102, the amplification of that locus will be greater and will produce a correspondingly larger amount of amplicons in block 104. In some embodiments, block 102 and 104 may be performed on the DNA sample within the same reaction tube.

It will be appreciated that the particular loci amplified in block 104 may depend on the particular trait(s) being investigated. For instance, one panel of loci may be used in embodiments of method 100 designed to identify a tissue source from which the DNA sample was derived, while another panel of loci may be used in embodiments of method 100 designed to identify an age of an organism from which the DNA sample was derived. For instance, as described further below (with reference to FIGS. 2-4), one illustrative embodiment of the method 100 used for tissue-typing the DNA sample may use a panel of ten loci, including eight target loci (in which methylation levels vary depending on tissue source) and two control loci (which undergo relatively consistent amplification regardless of tissue source).

It is contemplated that at least one of the plurality of loci amplified in block 104 will not contain a restriction site for the methylation-dependent endonuclease, thereby allowing that loci to act as a positive control locus for the assay. Without a restriction site for the methylation-dependent endonuclease, the positive control locus will not be digested at all in block 102 and, therefore, should be consistently amplified in block 104. In some embodiments, the plurality of loci may also include a negative control locus that is substantially un-methylated and thus substantially digested by the methylation-dependent endonuclease in block 102, irrespective of the trait associated with the DNA sample. In other words, in such embodiments, the negative control locus is chosen to be consistently digested in block 102 (and, therefore, to undergo only a relatively small amount of amplification, if any, in block 104), whether the DNA sample possesses or does not possess the particular trait under investigation (or regardless of which trait the DNA sample possesses from among a group of possible traits under investigation).

After block 104, method 100 may optionally proceed to block 106 in which amplicons having a length that is outside a predetermined range of nucleotides are removed from the plurality of amplicons produced in block 104. For instance, in some embodiments, amplicons that are less than fifty base pairs in length may be removed. Additionally or alternatively, in some embodiments, amplicons that are more than five-hundred base pairs in length may be removed. In other embodiments, amplicons that are more than one-hundred-and-fifty base pairs in length may be removed. It will be appreciated that the foregoing thresholds are illustrative and that the particular thresholds utilized for removing amplicons in block 106 (when used) will vary depending on the assay.

After block 106 (or, after block 104, in embodiments of method 100 not utilizing optional block 106), method 100 proceeds to block 108 in which the plurality of amplicons are sequenced using an MPS instrument to generate a plurality of sequence reads. Any number of commercially available MPS platforms may be used to sequence the amplicons in block 108. While MPS instruments may vary in their respective workflows, detection chemistries, data output, read length, and error rates, these instruments share the common ability to generate very large, sequence-based data sets that allow for immense multiplexing of a variety of forensic and investigative markers. As described further below (with reference to FIG. 2), it is contemplated that the method 100 may be integrated into a larger MPS workflow and be performed simultaneously with other MPS-based analyses of the same DNA sample (and/or additional DNA samples). By way of example, the method 100 may be incorporated into a combined MPS workflow in which STR allelotyping and/or single nucleotide polymorphism (SNP) allelotyping of the DNA sample are performed simultaneously with the method 100. In such embodiments, block 108 may involve sequencing additional amplicons (containing STRs and/or SNPs) at the same time the plurality of amplicons produced in block 104 are sequenced. In such embodiments, each of the amplicons being sequenced by the MPS instrument will typically be labeled with a unique nucleotide index (i.e., "barcode"), which will also be read by the MPS instrument to allow the resulting data to be de-multiplexed.

After block 108, method 100 proceeds to block 110 in which a sequence count for each of the plurality of loci amplified in block 104 is determined. In other words, block 110 involves analyzing the data generated by the MPS instrument in block 108 to quantify the amplification of each locus that occurred in block 104. Block 110 may use one or more bioinformatics techniques to determine which sequence reads correspond to which loci. In particular, block 110 may involve block 112 in which each of the plurality of sequence reads is compared to a plurality of reference sequences. Each of the reference sequences may be associated with one of the plurality of loci that was amplified in block 104. When a comparison of one of the sequence reads results in a "match" with one of the reference sequences, that sequence read may be added to the sequence count for the locus corresponding to that reference sequence. In some embodiments of block 112, a "match" between a sequence read and a reference sequence may be determined using an alignment algorithm (e.g., the Basic Local Alignment Search Tool, "BLAST"), which analyzes whether a particular sequence read sufficiently aligns to any of the reference sequences (allowing for a specified degree of mismatch). In other embodiments of block 112, a "match" between a sequence read and a reference sequence may be determined using an exact matching algorithm that requires all nucleotide bases in the sequence read to be identical to corresponding bases in the reference sequence to find a match. It is contemplated that other algorithms for comparing the sequence reads to the reference sequences may be utilized in other embodiments of method 100.

Figure 3:
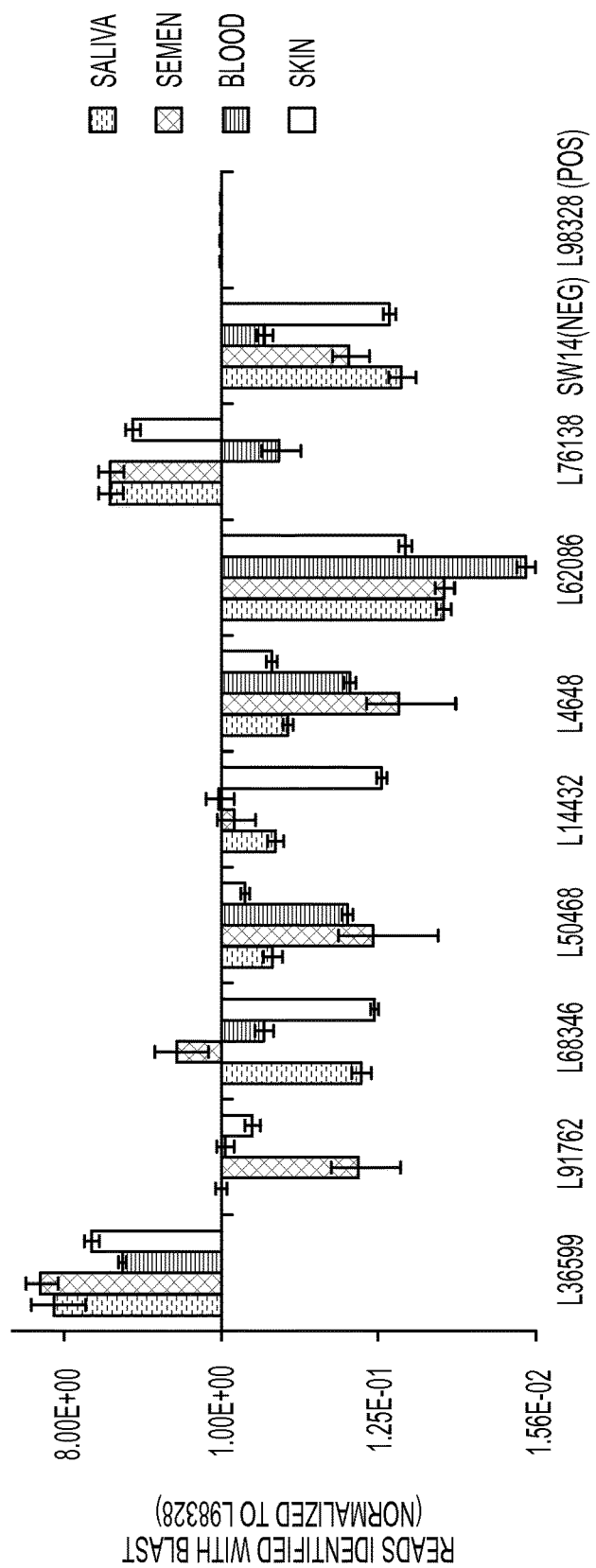
FIG. 3 is a graph illustrating epigenetic-based patterns detected via MPS, using the tissue typing workflow of FIG. 2.

After block 110, method 100 proceeds to block 114 in which the sequence count for each of the plurality of loci (determined in block 110) is normalized to the sequence count of the positive control locus (also determined in block 110). As discussed above, the positive control locus does not contain a restriction site for the methylation-dependent endonuclease, such that the positive control locus will not be digested in block 102 and should be consistently amplified in block 104. As such, the inclusion of the positive control locus allows for normalization of the data in block 114. It will be appreciated by those of skill in the art that this normalization approach is beneficial because it allows for a multitude of sample and assay multiplexing within single sequencer runs (in block 108). FIG. 3 illustrates the normalized sequence counts resulting from block 114 in one illustrative embodiment, which will be discussed further below.

After block 114, method 100 proceeds to block 116 in which a trait associated with the DNA sample is identified (e.g., a tissue source, a cell type, an age, a disease state or risk of disease, a response to environmental signals, a body mass index or an obesity state, an expression level of one or more genes, a physical characteristic, a drug response, an epigenetic inheritance, and/or another trait associated with the DNA sample). In particular, block 116 involves applying a classification algorithm to the normalized sequence counts determined in block 114 to identify the trait associated with the DNA sample. As noted above, the plurality of loci that are amplified in block 104 are chosen so that differential methylation patterns are represented in the normalized sequence counts determined in block 114, depending on the particular trait associated with the DNA sample being tested. Any suitable algorithm for classifying these differential methylation patterns as corresponding to particular traits may be used in block 116.

Figure 4:
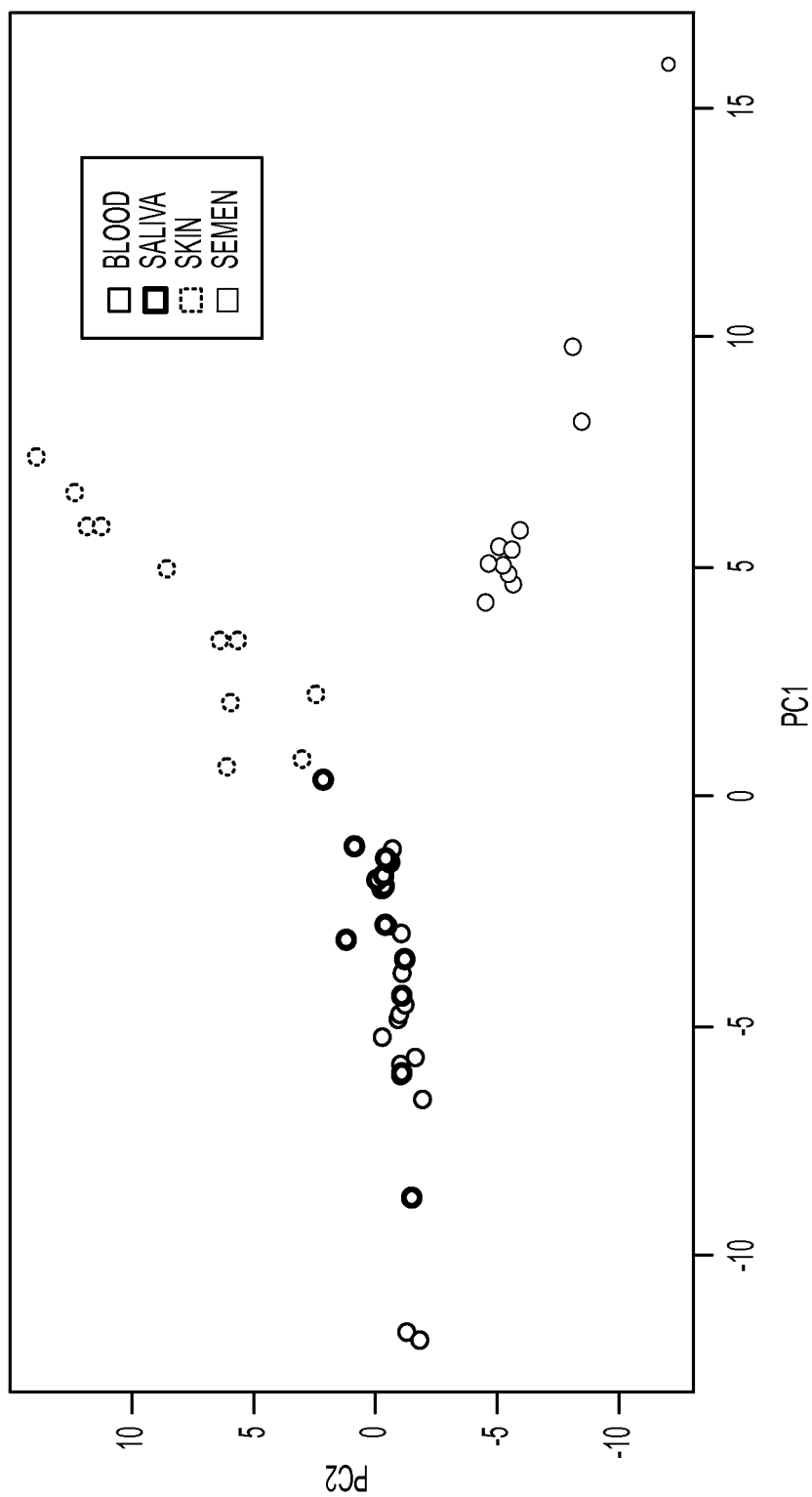
FIG. 4 is a graph illustrating clustering of tissue types generated by applying a k-Nearest Neighbor algorithm to the normalized sequence counts shown in FIG. 3.

In some embodiments, block 116 may involve applying a k-Nearest Neighbor (k-NN) algorithm to the normalized sequence counts determined in block 114. In particular, block 116 may involve computing un-weighted Euclidean distances of normalized sequence counts between the DNA sample (i.e., those determined in block 114) and a plurality of reference samples associated with different traits (i.e., normalized sequence counts previously determined for DNA samples known to be associated with particular traits). The trait associated with the DNA sample being tested may then be identified by finding the reference sample having the shortest Euclidean distance from the DNA sample under test. Using a k-NN algorithm, any number of reference samples can be chosen to compare to the DNA sample being tested. Advantages of the k-NN algorithm include being relatively quick (the analysis of block 116 took less than ten seconds in the illustrative embodiment described below) and not being prone to overtraining FIG. 4 illustrates the results from block 116 in one illustrative embodiment, which will be discussed in greater detail below.

Figure 2:
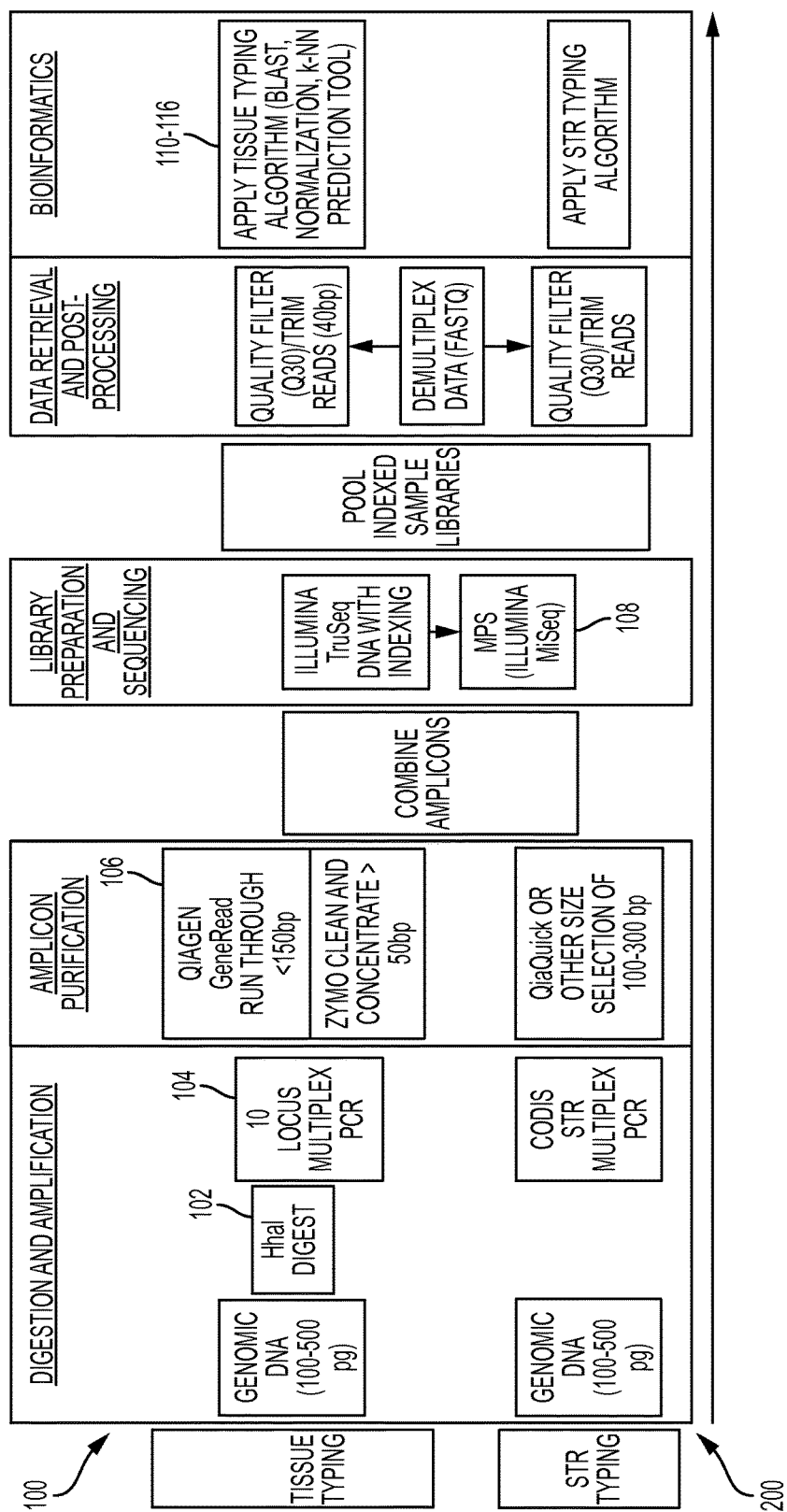
FIG. 2 is a simplified block diagram illustrating one embodiment of a combined MPS workflow including both a tissue typing workflow (following one illustrative embodiment of the method of FIG. 1) and a short tandem repeat allelotyping workflow.

Referring now to FIG. 2, one illustrative embodiment of the method 100 was implemented as tissue typing workflow 100. As shown in FIG. 2, the tissue typing workflow 100 is capable of being performed in parallel with an STR allelotyping workflow 200 as part of a combined MPS workflow. In particular, during this combined MPS workflow, the MPS instrument may simultaneously perform sequencing of both amplicons related to the tissue typing workflow 100 and amplicons related to the STR allelotyping workflow 200. It will be appreciated that, additionally or alternatively to the STR allelotyping workflow 200, many other types of MPS-based analyses may be performed in parallel with the tissue typing workflow 100. For instance, in other embodiments, the combined MPS workflow might involve an SNP allelotyping workflow and/or mitochondrial DNA (mtDNA) analysis.

In the tissue typing workflow 100 of the illustrative embodiment, sixteen DNA samples (1 ng each) were randomly chosen from among a pool of sixty-nine DNA samples of various donors. These sixteen DNA samples included four DNA samples derived from venous blood, four DNA samples derived from saliva, four DNA samples derived from semen, and four DNA samples derived from skin epidermis. All sixteen DNA samples were quantified using a Quantifiler Human DNA quantification kit and a 7900HT Sequence Detection System (both commercially available from Applied Biosystems of Carlsbad, Calif.).

Each DNA sample was digested with the methylation-dependent endonuclease HhaI and was PCR amplified in the same reaction tube. A set of eight target loci plus two control loci (for a total of ten loci, listed below in Table 1) were chosen for amplification. These particular loci were identified because they did not result in significant non-specific amplification products. L98328 (which has no HhaI restriction site) was used as the positive control locus, while SW14 (which was believed to have relatively low methylation levels in all relevant tissue types) was used as a negative control locus. It will be appreciated that, in other embodiments, additional and/or different loci from those listed in Table 1 may be used in the tissue typing workflow 100. For instance, in some embodiments, the tissue typing workflow 100 may use only a subset of the loci listed in Table 1. In other embodiments, the tissue typing workflow 100 may use additional loci beyond those listed in Table 1 (e.g., L26688).

TABLE 1

(SEQ ID NOS 1-20, respectively, in order of appearance)

| Locus | Chr# | Forward primer | Reverse primer | Amplicon Size (bp) | Conc. |
|---|---|---|---|---|---|
| L91762 | Chr12 | GCAGCAGGCCGC GGAGAAG | AGCAGCTGTGCC GGGCCAG | 66 | 0.2 µM |
| L68346 | Chr3 | CAGCAACAGCAC CCAGCTTG | CACAGGCTCAGT CGCGGATC | 70 | 0.2 µM |
| L50468 | Chr3 | AGGAAACCTCAG TAGCAAAATTG | GCGAGACTTTAG GTGTGCATC | 75 | 0.2 µM |
| L14432 | Chr22 | CGTAGGCTGCGG TGAGCTC | GATCCATGCCCG CTGGGATG | 75 | 0.2 µM |

TABLE 1-continued (SEQ ID NOS 1-20, respectively, in order of appearance)

| Locus | Chr# | Forward primer | Reverse primer | Amplicon Size (bp) | Conc. |
|---|---|---|---|---|---|
| L4648 | Chr1 | CAGCCTAGACGT CAAGTTACAG | ACGACCTCCGGA TCCAACTG | 80 | 0.2 µM |
| L62086 | Chr19 | GTGCATGGTGTC TGGTACTTC | GAAGCTCTCGTG GACTACTTG | 89 | 0.1 µM |
| L76138 | Chr19 | CAGCCTGCTCTT CACTGCAG | AGAGGCCGATGA AGCCGTAG | 100 | 0.2 µM |
| L36599 | Chr19 | AAGGGCAGAGTT CCGCTGTC | CGGATGCAGGAG GATCCTAG | 130 | 0.2 µM |
| SW14 (neg) | Chr7 | GCGAAGGAAGTG CTGGAGTC | GTTTCTTGAAAG GGCCAGACAC | 94 | 0.2 µM |
| L98328 (pos) | Chr11 | CAAAGTACTGGG GTTACAGGTG | GGATGAACCTTT AAGACATCATC | 97 | 0.2 µM |

The reaction tube in which digestion and amplification were conducted contained 80 U of HhaI (commercially available from New England Biolabs of Ipswich, Mass.), 10 µl of 5× PowerPlex Fusion Master Mix DP207A, 10 µg BSA (also commercially available from New England Biolabs), 0.1-0.3 µM of each primer listed in Table 1 above, and ddH$_2$O in a total volume of 50 µl. Digestion and amplification was performed in a GeneAmp PCR System 9700 thermal cycler (commercially available from Applied Biosystems) with the following program: 37° C. for 15 minute (for HhaI digestion); 95° C. for 11 minute; 28 cycles of 94° C. for 15 seconds, 59° C. for 15 seconds, and 72° C. for 1 minute; and a final extension step of 72° C. for 1 minute.

The amplicons produced by the sixteen DNA samples were made into sequencing libraries and given unique 6-nucleotide indexes (i.e., "barcodes") with TruSeq DNA (commercially available from Illumina of San Diego, Calif.) using the manufacturer's recommended protocol for amplicon libraries. As shown in FIG. 2, the samples were size selected and purified using GeneRead Size Selection kit (commercially available from Qiagen of Valencia, Calif.) to remove amplicons greater than one-hundred-and-fifty base pairs and using DNA Clean and Concentrator-5 (commercially available from Zymo of Irvine, Calif.) to remove low molecular weight DNA fragments less than fifty base pairs. Purified products were quantified for sequence-ready products using a qPCR based Library Quantification Kit (commercially available from KAPA BioSystems of Wilmington, Mass.), pooled in equimolar amounts, and spiked with PhiX Control v3 (commercially available from Illumina) to increase sequence diversity and obtain higher quality data. MPS was performed on an Illumina MiSeq instrument with MiSeq V2 sequencing chemistries (commercially available from Illumina) and a single-end fifty base pair protocol. Demultiplexing of sample libraries based on Illumina barcodes was performed post-sequencing using the Illumina MiSeq software. Raw sequence data in the FASTQ file format was created for each sample library and used in downstream analysis.

Raw sequence reads contained in the FASTQ files were quality filtered to average (Q30) and then trimmed to the first forty nucleotides and compared to reference sequences using BLAST (with a word size of 15, 97% identity, and e-score of 1e−10). BLAST output files were parsed and the number of sequence reads corresponding to each locus was determined. Sequence counts identified in BLAST were normalized to the sequence count from the positive control loci (L98328). A k-NN algorithm was invoked in the R-statistical programming environment to compute un-weighted Euclidean distances of continuous variables (normalized sequence reads) to cluster the tested DNA samples into group assignments.

Using the single-end fifty base pair sequencing routine on the MiSeq instrument with V2 chemistries (as described above), a single run produced $3.16 \times 10^7$ total sequence reads for the sixteen samples, with an average of over three million sequence reads per sample. An average of 32.7% of the sequence reads passed the quality filter and 40.8% of the quality filtered sequence reads were assigned to one of the ten loci using the BLAST algorithm (for an average of $4.95 \times 10^5$ "matched" sequence reads per sample). These results are summarized in Table 2 below.

TABLE 2

|  | Reads In Raw File | Reads After Quality Filtering | % Reads Passing Quality Filter | BLAST Hits | % BLAST Hits |
|---|---|---|---|---|---|
| Sample_028 | 1.81E+06 | 5.00E+05 | 27.7 | 2.69E+05 | 53.8 |
| Sample_080 | 1.88E+06 | 7.63E+05 | 40.6 | 3.05E+05 | 39.9 |
| Sample_U12 | 1.78E+06 | 6.33E+05 | 35.6 | 3.43E+05 | 54.1 |
| Sample_U23 | 1.45E+06 | 5.69E+05 | 39.3 | 3.27E+05 | 57.5 |
| Sample_U34 | 1.57E+06 | 4.37E+05 | 27.9 | 2.70E+05 | 61.8 |
| Sample_U35 | 2.00E+06 | 5.71E+05 | 28.5 | 2.33E+05 | 40.8 |
| Sample_U46 | 1.32E+06 | 1.28E+05 | 9.7 | 8.15E+04 | 63.5 |
| Sample_U70 | 1.57E+06 | 4.50E+05 | 28.7 | 1.97E+05 | 43.8 |
| Sample_card5 | 1.23E+06 | 3.99E+05 | 32.4 | 1.15E+05 | 28.8 |
| Sample_card8 | 1.19E+06 | 4.12E+05 | 34.6 | 1.04E+05 | 25.3 |
| Sample_card10 | 7.46E+06 | 2.68E+06 | 35.9 | 9.15E+05 | 34.2 |
| Sample_card15 | 1.04E+06 | 3.33E+05 | 31.9 | 1.16E+05 | 34.8 |
| Sample_Skin10413A | 9.92E+05 | 2.69E+05 | 27.1 | 1.12E+05 | 41.6 |
| Sample_Skin10413B | 3.64E+06 | 1.19E+06 | 32.7 | 4.61E+05 | 38.7 |
| Sample_Skin10913 | 1.20E+06 | 4.10E+05 | 34.0 | 1.74E+05 | 42.6 |
| Sample_Skin11013A | 1.42E+06 | 5.72E+05 | 40.2 | 1.88E+05 | 33.0 |
| Total | 3.16E+07 | 1.03E+07 | — | 4.21E+06 | — |
| Average | 3.71E+06 | 1.21E+06 | 32.7 | 4.95E+05 | 40.8 |

The sequence count associated with each locus was normalized to the corresponding sequence count of the positive control locus, L98328. These results are shown as a bar graph in FIG. 3, in which the y-axis shows the normalized sequence count for each tissue type (±standard error) plotted as log base 2. Measurable differences with low deviation were observed in methylated loci dependent on the tissue type. For example, the L68346A locus showed higher levels of methylation in semen, while saliva and skin demonstrated markedly lower methylation, as shown in FIG. 3. A k-NN algorithm was used to assign samples into the tissue source groups based on the normalized sequence reads, as illustrated in FIG. 4 in a principal component analysis (PCA). In the illustrative embodiment just described, the concordance rate for true source to the k-NN determined source was 15/16 (see Table 3 below). A single semen sample (Sample_U35) was misidentified as originating from blood. Using the k-NN algorithm, the source of 93.8% of the tissue samples was correctly identified and the false positive rate was 0.021 (see Table 4 below). Furthermore, it is believed, based on the current dataset, that it may be possible to remove all loci except for L91762 and still achieve 93.8% accuracy.

TABLE 3

| Tissue Source | | | | k-NN |
|---|---|---|---|---|
| Saliva | Blood | Skin | Semen | Classification |
| 4 | 0 | 0 | 0 | Saliva |
| 0 | 4 | 0 | 1 | Blood |
| 0 | 0 | 4 | 0 | Skin |
| 0 | 0 | 0 | 3 | Semen |

TABLE 4

| Tissue Source | Rate of True Positive | Rate of False Positive |
|---|---|---|
| Saliva | 1 | 0 |
| Blood | 1 | 0.083 |
| Skin | 1 | 0 |

TABLE 4-continued

| Tissue Source | Rate of True Positive | Rate of False Positive |
|---|---|---|
| Semen | 0.75 | 0 |
| Weight Averages | 0.938 | 0.021 |

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A method comprising:
digesting a deoxyribonucleic acid (DNA) sample with a methylation-dependent endonuclease;
amplifying a plurality of loci of the digested DNA sample using a multiplex polymerase chain reaction (PCR) to produce a plurality of amplicons, at least one of the plurality of loci being a positive control locus that does not contain a restriction site for the methylation-dependent endonuclease, the positive control locus being a 97 base pair amplicon located on chromosome 11 between SEQ ID NO: 19 and SEQ ID NO: 20;
sequencing the plurality of amplicons using a massively parallel sequencing (MPS) instrument to generate a plurality of sequence reads;
determining a sequence count for each of the plurality of loci by comparing each of the plurality of sequence reads to a plurality of reference sequences, each of the plurality of reference sequences being associated with one of the plurality of loci;
normalizing the sequence count for each of the plurality of loci to the sequence count of the positive control locus; and
identifying a trait associated with the DNA sample by applying a classification algorithm to the normalized sequence counts.

2. The method of claim 1, wherein comparing each of the plurality of sequence reads to the plurality of reference sequences comprises determining whether each of the plurality of sequence reads sufficiently aligns with any of the plurality of reference sequences.

3. The method of claim 1, wherein comparing each of the plurality of sequence reads to the plurality of reference sequences comprises determining whether each of the plurality of sequence reads exactly matches any of the plurality of reference sequences.

4. The method of claim 1, wherein the multiplex PCR uses unlabeled primers.

5. The method of claim 1, further comprising removing amplicons having a length that is outside a predetermined range prior to sequencing the plurality of amplicons.

6. The method of claim 5, wherein the predetermined range is about 50 base pairs to about 500 base pairs.

7. The method of claim 1, wherein applying the classification algorithm comprises applying a k-Nearest Neighbor (k-NN) algorithm.

8. The method of claim 7, wherein applying the k-NN algorithm comprises computing un-weighted Euclidean distances of normalized sequence counts between the DNA sample and a plurality of reference samples associated with different traits.

9. The method of claim 1, further comprising:
labeling each of the plurality of amplicons with a unique nucleotide index;
mixing the plurality of amplicons with additional amplicons that have each been labeled with a unique nucleotide index; and
sequencing the additional amplicons using the MPS instrument at the same time as sequencing the plurality of amplicons.

10. The method of claim 9, wherein the additional amplicons contain short tandem repeats that are used to allelotype the DNA sample.

11. The method of claim 9, wherein the additional amplicons contain single nucleotide polymorphisms that are used to allelotype the DNA sample.

12. The method of claim 1, wherein at least one of the plurality of loci is a negative control locus that is substantially digested by the methylation-dependent endonuclease irrespective of the trait associated with the DNA sample.

13. The method of claim 12, wherein the negative control locus is a 94 base pair amplicon located on chromosome 7 between SEQ ID NO: 17 and SEQ ID NO: 18.

14. The method of claim 1, wherein the methylation-dependent endonuclease is Hha1.

15. The method of claim 1, wherein the plurality of loci comprise one or more of:
a 66 base pair amplicon located on chromosome 12 between SEQ ID NO: 1 and SEQ ID NO: 2,
a 70 base pair amplicon located on chromosome 3 between SEQ ID NO: 3 and SEQ ID NO: 4,
a 75 base pair amplicon located on chromosome 3 between SEQ ID NO: 5 and SEQ ID NO: 6,
a 75 base pair amplicon located on chromosome 22 between SEQ ID NO: 7 and SEQ ID NO: 8, an 80 base pair amplicon located on chromosome 1 between SEQ ID NO: 9 and SEQ ID NO: 10,
an 89 base pair amplicon located on chromosome 19 between SEQ ID NO: 11 and SEQ ID NO: 12,
a 100 base pair amplicon located on chromosome 19 between SEQ ID NO: 13 and SEQ ID NO: 14, and
a 130 base pair amplicon located on chromosome 19 between SEQ ID NO: 15 and SEQ ID NO: 16.

16. The method of claim 1, wherein the plurality of loci consist of:
a 66 base pair amplicon located on chromosome 12 between SEQ ID NO: 1 and SEQ ID NO: 2,
a 70 base pair amplicon located on chromosome 3 between SEQ ID NO: 3 and SEQ ID NO: 4,
a 75 base pair amplicon located on chromosome 3 between SEQ ID NO: 5 and SEQ ID NO: 6,
a 75 base pair amplicon located on chromosome 22 between SEQ ID NO: 7 and SEQ ID NO: 8,
an 80 base pair amplicon located on chromosome 1 between SEQ ID NO: 9 and SEQ ID NO: 10,
an 89 base pair amplicon located on chromosome 19 between SEQ ID NO: 11 and SEQ ID NO: 12,
a 100 base pair amplicon located on chromosome 19 between SEQ ID NO: 13 and SEQ ID NO: 14,
a 130 base pair amplicon located on chromosome 19 between SEQ ID NO: 15 and SEQ ID NO: 16, and
a 94 base pair region located on chromosome 7 between SEQ ID NO: 17 and SEQ ID NO: 18.

17. The method of claim 1, wherein identifying the trait associated with the DNA sample comprises identifying a tissue source from which the DNA sample was derived.

18. The method of claim 17, wherein identifying the tissue source from which the DNA sample was derived comprises determining whether the tissue source is blood, skin, saliva, or semen.

19. The method of claim 1, wherein identifying the trait associated with the DNA sample comprises identifying a cell type from which the DNA sample was derived.

20. The method of claim 1, wherein identifying the trait associated with the DNA sample comprises identifying an age of an organism from which the DNA sample was derived.

21. The method of claim 1, wherein identifying the trait associated with the DNA sample comprises identifying a disease state or risk of disease of an organism from which the DNA sample was derived.

22. The method of claim 1, wherein identifying the trait associated with the DNA sample comprises identifying a response to environmental signals of an organism from which the DNA sample was derived.

23. The method of claim 1, wherein identifying the trait associated with the DNA sample comprises identifying a body mass index or an obesity state of an organism from which the DNA sample was derived.

24. The method of claim 1, wherein identifying the trait associated with the DNA sample comprises identifying an expression level of one or more genes in an organism from which the DNA sample was derived.

25. The method of claim 1, wherein identifying the trait associated with the DNA sample comprises identifying a physical characteristic of an organism from which the DNA sample was derived.

26. The method of claim 1, wherein identifying the trait associated with the DNA sample comprises identifying a drug response of an organism from which the DNA sample was derived.

27. The method of claim 1, wherein identifying the trait associated with the DNA sample comprises identifying an epigenetic inheritance of an organism from which the DNA sample was derived.

28. The method of claim 1, wherein identifying the trait associated with the DNA sample comprises identifying whether the DNA sample was synthesized in vitro.

29. One or more non-transitory, computer-readable media comprising a plurality of instructions that, when executed by one or more processors, causes the one or more processors to:
determine a sequence count for each of a plurality of loci of a digested deoxyribonucleic acid (DNA) sample by comparing each of a plurality of sequence reads to a plurality of reference sequences, the plurality of sequence reads resulting from massively parallel sequencing (MPS) of amplification products of a multiplex polymerase chain reaction (PCR) applied to the plurality of loci, wherein
(i) the DNA sample has been digested with a methylation-dependent endonuclease;
(ii) at least one of the plurality of loci is a positive control locus that does not contain a restriction site for the methylation-dependent endonuclease, the positive control locus being a 97 base pair amplicon located on chromosome 11 between SEQ ID NO: 19 and SEQ ID NO: 20; and
(iii) each of the plurality of reference sequences is associated with one of the plurality of loci;
normalize the sequence count for each of the plurality of loci to the sequence count of the positive control locus; and
apply a classification algorithm to the normalized sequence counts to identify a trait associated with the DNA sample.

30. The one or more non-transitory, computer-readable media of claim 29, wherein the plurality of instructions, when executed by one or more processors, causes the one or more processors to determine whether each of the plurality of sequence reads sufficiently aligns with any of the plurality of reference sequences to determine the sequence count for each of the plurality of loci.

31. The one or more non-transitory, computer-readable media of claim 29, wherein the plurality of instructions, when executed by one or more processors, causes the one or more processors to determine whether each of the plurality of sequence reads exactly matches any of the plurality of reference sequences to determine the sequence count for each of the plurality of loci.

32. The one or more non-transitory, computer-readable media of claim 29, wherein the plurality of instructions, when executed by one or more processors, causes the one or more processors to compute un-weighted Euclidean distances of normalized sequence counts between the DNA sample and a plurality of reference samples associated with different traits as part of the classification algorithm.

33. The method of claim 1, wherein the one or more loci of the plurality of loci are located on chromosomes 1, 3, 7, 11, 12, 19, 22, or combinations thereof.

* * * * *